United States Patent
Farwick et al.

(10) Patent No.: US 7,029,904 B2
(45) Date of Patent: Apr. 18, 2006

(54) NUCLEOTIDE SEQUENCES WHICH CODE FOR THE DEP34 GENE

(75) Inventors: Mike Farwick, Bielefeld (DE); Klaus Huthmacher, Gelnhausen (DE); Walter Pfefferle, Halle (Westf.) (DE); Thomas Hermann, Bielefeld (DE); Brigitte Bathe, Salzkotten (DE)

(73) Assignee: Degussa AG, (DE)

( * ) Notice: Subject to any disclaimer, the term of this patent is extended or adjusted under 35 U.S.C. 154(b) by 160 days.

(21) Appl. No.: 09/946,763

(22) Filed: Sep. 6, 2001

(65) Prior Publication Data

US 2002/0106757 A1    Aug. 8, 2002

(30) Foreign Application Priority Data

Sep. 9, 2000 (DE) .................. 100 44 708
Mar. 15, 2001 (DE) .................. 101 12 429

(51) Int. Cl.
*C12N 1/20* (2006.01)
*C12N 15/00* (2006.01)
*C07H 21/04* (2006.01)

(52) U.S. Cl. .............. 435/252.33; 435/320.1; 536/23.7; 536/24.32

(58) Field of Classification Search ........... 536/23.1, 536/23.7, 24.3, 24.33, 23.2; 435/320.1, 252.3, 435/254.11, 419, 325, 252.32, 252.33
See application file for complete search history.

(56) References Cited

U.S. PATENT DOCUMENTS 6,822,084 B1 * 11/2004 Pompejus et al. ......... 536/23.7

2002/0197605 A1 * 12/2002 Nakagawa et al. ............ 435/6

FOREIGN PATENT DOCUMENTS

| EP | 0 435 132 | | 7/1991 |
|----|-----------|---|--------|
| WO | WO 00/22430 | * | 4/2000 |
| WO | WO 01/00804 | | 1/2001 |
| WO | EP 1 108 790 A | | 6/2001 |

OTHER PUBLICATIONS

Jan. 12, 1999, Seeger K J et al., "Streptomyces coelicolor cosmid 9C7." Database accession No. AL035161.
Eggeling L et al., "L-Glutamate and L-lysine: traditional products with impetuous developments", Applied Microbiology and Biotechnology, vol. 52, No. 2, 1999, pp. 146-153.
Kramer R: "Genetic and physiological approaches for the production of amino acids" Journal of Biotechnology, vol. 45, No. 1, Feb. 12, 1996, pp. 1-21.

* cited by examiner

*Primary Examiner*—David J. Steadman
(74) *Attorney, Agent, or Firm*—Smith, Gambrell & Russell, LLP

(57) ABSTRACT

The invention relates to an isolated polynucleotide from *Corynebacterium glutamicum* having a polynucleotide sequence which codes for the dep34 efflux protein, and a host-vector system having a coryneform host bacterium in which the dep34 gene is present in attenuated form and a vector which carries at least the dep34 gene according to SEQ ID NO: 1, and the use of polynucleotides which comprise the sequences according to the invention as hybridization probes.

5 Claims, 1 Drawing Sheet

Figure 1: Plasmid pCR2.1dep34int
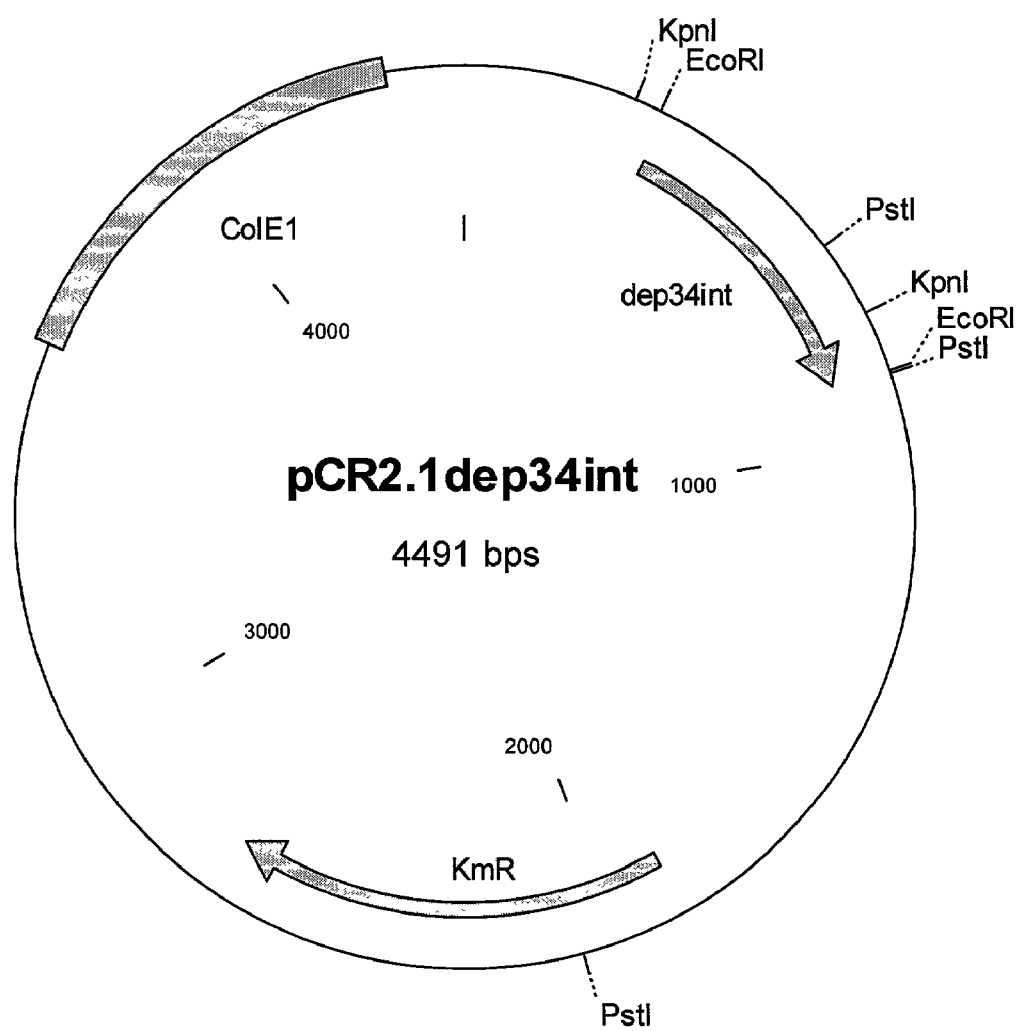

NUCLEOTIDE SEQUENCES WHICH CODE FOR THE DEP34 GENE

BACKGROUND OF THE INVENTION

The invention provides nucleotide sequences from coryneform bacteria which code for the dep34 gene and a process for the fermentative preparation of amino acids using bacteria in which the dep34 gene is attenuated. All references cited herein are expressly incorporated by reference. Incorporation by reference is also designated by the term "I.B.R." following any citation.

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

The invention provides new measures for improved fermentative preparation of amino acids.

BRIEF SUMMARY OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from coryneform bacteria, comprising a polynucleotide sequence which codes for the dep34 gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of the efflux protein Dep34.

The invention also provides the above-mentioned polynucleotide, this preferably being a DNA which is capable of replication, comprising:

(i) the nucleotide sequence, shown in SEQ ID No. 1, or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i).

The invention also provides:

a polynucleotide, in particular DNA, which is capable of replication and comprises the nucleotide sequence as shown in SEQ ID No. 1;

a polynucleotide which codes for a polypeptide which comprises the amino acid sequence as shown in SEQ ID No. 2;

a vector containing parts of the polynucleotide according to the invention, but at least 15 successive nucleotides of the sequence claimed, and coryneform bacteria in which the dep34 gene is attenuated, in particular by an insertion or deletion.

The invention also provides polynucleotides, which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No. 1 or a fragment thereof, and isolation of the polynucleotide sequence mentioned.

BRIEF DESCRIPTION OF THE FIGURES

FIG. 1: Map of the plasmid pCR2.1dep34int.

The abbreviations and designations used have the following meaning.

| | |
|---|---|
| KmR: | Kanamycin resistance gene |
| KpnI: | Cleavage site of the restriction enzyme KpnI |
| EcoRI: | Cleavage site of the restriction enzyme EcoRI |
| PstI: | Cleavage site of the restriction enzyme PstI |
| dep34int: | Internal fragment of the dep34 gene |
| ColE1: | Replication origin of the plasmid ColE1 |

DETAILED DESCRIPTION OF THE INVENTION

Polynucleotides which comprise the sequences according to the invention are suitable as hybridization probes for RNA, cDNA and DNA, in order to isolate, in the full length, nucleic acids or polynucleotides or genes which code for the efflux protein Dep34 or to isolate those nucleic acids or polynucleotides or genes which have a high similarity with the sequence of the dep34 gene. They are also suitable for incorporation into so-called "arrays", "micro arrays" or "DNA chips" in order to detect and determine the corresponding polynucleotides.

Polynucleotides which comprise the sequences according to the invention are furthermore suitable as primers with the aid of which DNA of genes which code for the efflux protein Dep34 can be prepared by the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the efflux protein Dep34 and also those which are at least 70% to 80%, preferably at least 81% to 85%, particularly preferably at least 86% to 90% and very particularly preferably at least 91%, 93%, 95%, 97% or 99% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the dep34 gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

The microorganisms provided by the present invention can prepare amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The new dep34 gene from *C. glutamicum* which codes for the efflux protein Dep34 has been isolated.

To isolate the dep34 gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164) I.B.R. in the *E. coli* K-12 strain NM554 (Raleigh et al., 1988, Nucleic Acids Research 16:1563–1575) I.B.R.

Börmann et al. (Molecular Microbiology 6(3), 317–326)) (1992)) I.B.R. in turn describe a gene library of *C. glutamicum* ATCC13032 using the cosmid pHC79 (Hohn and Collins, 1980, Gene 11, 291–298 I.B.R.).

To prepare a gene library of *C. glutamicum* in *E. coli* it is also possible to use plasmids such as pBR322 (Bolivar, 1979, Life Sciences, 25, 807–818 I.B.R.) or pUC9 (Vieira et al., 1982, Gene, 19:259–268 I.B.R.). Suitable hosts are, in particular, those *E. coli* strains which are restriction- and recombination-defective, such as, for example, the strain DH5αmcr, which has been described by Grant et al. (Proceedings of the National Academy of Sciences USA, 87 (1990) 4645–4649 I.B.R.). The long DNA fragments cloned with the aid of cosmids or other λ vectors can then in turn be subcloned and subsequently sequenced in the usual vectors which are suitable for DNA sequencing, such as is described e.g. by Sanger et al. (Proceedings of the National Academy of Sciences of the United States of America, 74:5463–5467, 1977) I.B.R.

The resulting DNA sequences can then be investigated with known algorithms or sequence analysis programs, such as e.g. that of Staden (Nucleic Acids Research 14, 217–232 (1986)) I.B.R., that of Marck (Nucleic Acids Research 16, 1829–1836 (1988)) I.B.R. or the GCG program of Butler (Methods of Biochemical Analysis 39, 74–97 (1998)) I.B.R.

The new DNA sequence of *C. glutamicum* which codes for the dep34 gene and which, as SEQ ID No. 1, is a constituent of the present invention has been found. The amino acid sequence of the corresponding protein has furthermore been derived from the present DNA sequence by the methods described above. The resulting amino acid sequence of the dep34 gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology 41: 255–260 (1991)) I.B.R. The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996 I.B.R.).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995 I.B.R.) a temperature of approx. 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984 I.B.R.) and in Newton and Graham: PCR (Spektrum Akademischer Verlag, Heidelberg, Germany, 1994 I.B.R.).

It has been found that coryneform bacteria produce amino acids in an improved manner after attenuation of the dep34 gene.

To achieve an attenuation, either the expression of the dep34 gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246 I.B.R., in Boyd and Murphy (Journal of Bacteriology 170: 5949 (1988)) I.B.R., in Voskuil and Chambliss (Nucleic Acids Research 26: 3548 (1998) I.B.R., in Jensen and Hammer (Biotechnology and Bioengineering 58: 191 (1998)) I.B.R., in Patek et al. (Microbiology 142: 1297 (1996)) I.B.R., Vasicova et al. (Journal of Bacteriology 181: 6188 (1999)) I.B.R. and in known textbooks of genetics and molecular biology, such as e.g. the textbook by Knippers ("Molekulare Genetik [Molecular Genetics]", 6th edition, Georg Thieme Verlag, Stuttgart, Germany, 1995) I.B.R. or that by Winnacker ("Gene und Klone [Genes and Clones]", VCH Verlagsgesellschaft, Weinheim, Germany, 1990) I.B.R.

Mutations which lead to a change or reduction in the catalytic properties of enzyme proteins are known from the prior art; examples which may be mentioned are the works by Qiu and Goodman (Journal of Biological Chemistry 272: 8611–8617 (1997)) I.B.R., Sugimoto et al. (Bioscience Biotechnology and Biochemistry 61: 1760–1762 (1997)) I.B.R. and Möckel ("Die Threonindehydratase aus *Corynebacterium glutamicum*: Aufhebung der allosterischen Regulation und Struktur des Enzyms [Threonine dehydratase from *Corynebacterium glutamicum*: Canceling the allosteric regulation and structure of the enzyme]", Reports from the Jülich Research Center, Jül-2906, ISSN09442952, Jülich, Germany, 1994) I.B.R. Summarizing descriptions can be found in known textbooks of genetics and molecular biology, such as e.g. that by Hagemann ("Allgemeine Genetik [General Genetics]", Gustav Fischer Verlag, Stuttgart, 1986) I.B.R.

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995) I.B.R., that by Winnacker ("Gene und Klone [Genes and Clones]", VCH Verlagsgesellschaft, Weinheim, Germany, 1990) I.B.R. or that by Hagemann ("Allgemeine Genetik [General Genetics]", Gustav Fischer Verlag, Stuttgart, 1986) I.B.R.

A common method of mutating genes of C. glutamicum is the method of "gene disruption" and "gene replacement" described by Schwarzer and Pühler (Bio/Technology 9, 84–87 (1991)) I.B.R.

In the method of gene disruption a central part of the coding region of the gene of interest is cloned in a plasmid vector which can replicate in a host (typically E. coli), but not in C. glutamicum. Possible vectors are, for example, pSUP301 (Simon et al., Bio/Technology 1, 784–791 (1983)) I.B.R., pK18mob or pK19mob (Schäfer et al., Gene 145, 69–73 (1994) I.B.R.), pK18mobsacB or pK19mobsacB (Jäger et al., Journal of Bacteriology 174: 5462–65 (1992) I.B.R.), pGEM-T (Promega corporation, Madison, Wis., USA), pCR2.1-TOPO (Shuman (1994). Journal of Biological Chemistry 269:32678–84 I.B.R.; U.S. Pat. No. 5,487,993 I.B.R.), pCR®Blunt (Invitrogen, Groningen, Holland; Bernard et al., Journal of Molecular Biology, 234: 534–541 (1993) I.B.R.) or pEM1 (Schrumpf et al, 1991, Journal of Bacteriology 173:4510–4516 I.B.R.). The plasmid vector which contains the central part of the coding region of the gene is then transferred into the desired strain of C. glutamicum by conjugation or transformation. The method of conjugation is described, for example, by Schäfer et al. (Applied and Environmental Microbiology 60, 756–759 (1994)) I.B.R. Methods for transformation are described, for example, by Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) I.B.R. to eliminate the recA gene of C. glutamicum.

In the method of "gene replacement", a mutation, such as e.g. a deletion, insertion or base exchange, is established in vitro in the gene of interest. The allele prepared is in turn cloned in a vector which is not replicative for C. glutamicum and this is then transferred into the desired host of C. glutamicum by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) I.B.R. to eliminate the pyc gene of C. glutamicum by a deletion.

A deletion, insertion or a base exchange can be incorporated into the dep34 gene in this manner.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the attenuation of the dep34 gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

Thus, for the preparation of L-amino acids, in addition to attenuation of the dep34 gene, at the same time one or more of the genes chosen from the group consisting of the dapA gene which codes for dihydrodipicolinate synthase (EP-B 0 197 335 I.B.R.), the gap gene which codes for glyceraldehyde 3-phosphate dehydrogenase (Eikmanns (1992), Journal of Bacteriology 174:6076–6086 I.B.R.), the tpi gene which codes for triose phosphate isomerase (Eikmanns (1992), Journal of Bacteriology 174:6076–6086 I.B.R.), the pgk gene which codes for 3-phosphoglycerate kinase (Eikmanns (1992), Journal of Bacteriology 174:6076–6086 I.B.R.), the zwf gene which codes for glucose 6-phosphate dehydrogenase (JP-A-09224661 I.B.R.), the pyc gene which codes for pyruvate carboxylase (DE-A-198 31 609 I.B.R.), the mqo gene which codes for malate-quinone oxidoreductase (Molenaar et al., European Journal of Biochemistry 254, 395–403 (1998) I.B.R.), the lysC gene which codes for a feed-back resistant aspartate kinase (Accession No. P26512; EP-B-0387527 I.B.R.; EP-A-0699759 I.B.R.; WO 00/63388 I.B.R.), the lysE gene which codes for lysine export (DE-A-195 48 222 I.B.R.), the hom gene which codes for homoserine dehydrogenase (EP-A 0131171 I.B.R.), the ilvA gene which codes for threonine dehydratase (Möckel et al., Journal of Bacteriology (1992) 8065–8072) I.B.R.) or the ilvA(Fbr) allele which codes for a "feed back resistant" threonine dehydratase (Möckel et al., (1994) Molecular Microbiology 13: 833–842 I.B.R.), the ilvBN gene which codes for acetohydroxy-acid synthase (EP-B 0356739 I.B.R.), the ilvD gene which codes for dihydroxy-acid dehydratase (Sahm and Eggeling (1999) Applied and Environmental Microbiology 65: 1973–1979 I.B.R.), the zwa1 gene which codes for the Zwa1 protein (DE: 19959328.0 I.B.R., DSM 13115)

can be enhanced, in particular over-expressed.

It may furthermore be advantageous for the production of amino acids, in addition to attenuation of the dep34 gene, at the same time for one or more of the genes chosen from the group consisting of the pck gene which codes for phosphoenol pyruvate carboxykinase (DE 199 50 409.1 I.B.R., DSM 13047), the pgi gene which codes for glucose 6-phosphate isomerase (U.S. Pat. No. 6,586,214 I.B.R., DSM 12969), the poxB gene which codes for pyruvate oxidase (DE:1995 1975.7 I.B.R., DSM 13114), the zwa2 gene which codes for the Zwa2 protein (DE: 19959327.2 I.B.R., DSM 13113) to be attenuated, in particular for the expression thereof to be reduced.

In addition to the attenuation of the dep34 gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982 I.B.R.).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991) I.B.R.) or in the textbook by Storhas (Bioreaktoren und periphere Einrichtungen [Bioreactors and Peripheral Equipment] (Vieweg Verlag, Braunschweig/Wiesbaden, 1994) I.B.R.).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) I.B.R. by anion exchange chromatography with subsequent ninhydrin derivation, or it can be carried out by reversed phase HPLC, for example as described by Lindroth et al. (Analytical Chemistry (1979) 51: 1167–1174) I.B.R.

The process according to the invention is used for fermentative preparation of amino acids.

The following microorganism was deposited on May 03, 2001 as a pure culture at the Deutsche Sammlung für Mikroorganismen und Zellkulturen (DSMZ=German Collection of Microorganisms and Cell Cultures, Mascheroder Weg 1b D-38124 Braunschweig, Germany) in accordance with the Budapest Treaty:

Escherichia coli top10/pCR2.1dep34int as DSM 14144.

The present invention is explained in more detail in the following with the aid of embodiment examples.

The isolation of plasmid DNA from Escherichia coli and all techniques of restriction, Klenow and alkaline phosphatase treatment were carried out by the method of Sambrook et al. (Molecular Cloning. A Laboratory Manual, 1989, Cold Spring Harbour Laboratory Press, Cold Spring Harbor, N.Y., USA) I.B.R. Methods for transformation of Escherichia coli are also described in this handbook.

The composition of the usual nutrient media, such as LB or TY medium, can also be found in the handbook by Sambrook et al.

EXAMPLE 1

Preparation of a Genomic Cosmid Gene Library from C. glutamicum ATCC 13032

Chromosomal DNA from C. glutamicum ATCC 13032 was isolated as described by Tauch et al. (1995, Plasmid 33:168–179) I.B.R. and partly cleaved with the restriction enzyme Sau3AI (Amersham Pharmacia, Freiburg, Germany, Product Description Sau3AI, Code no. 27-0913-02 I.B.R.). The DNA fragments were dephosphorylated with shrimp alkaline phosphatase (Roche Molecular Biochemicals, Mannheim, Germany, Product Description SAP, Code no. 1758250 I.B.R.). The DNA of the cosmid vector SuperCos1 (Wahl et al. (1987), Proceedings of the National Academy of Sciences, USA 84:2160–2164 I.B.R.), obtained from Stratagene (La Jolla, USA, Product Description SuperCos1 Cosmid Vector Kit, Code no. 251301 I.B.R.) was cleaved with the restriction enzyme XbaI (Amersham Pharmacia, Freiburg, Germany, Product Description XbaI, Code no. 27-0948-02 I.B.R.) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04 I.B.R.). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04 I.B.R.). The ligation mixture was then packed in phages with the aid of Gigapack II XL Packing Extract (Stratagene, La Jolla, USA, Product Description Gigapack II XL Packing Extract, Code no. 200217 I.B.R.).

For infection of the E. coli strain NM554 (Raleigh et al. 1988, Nucleic Acid Res. 16:1563–1575 I.B.R.) the cells were taken up in 10 mM MgSO$_4$ and mixed with an aliquot of the phage suspension. The infection and titering of the cosmid library were carried out as described by Sambrook et al. (1989, Molecular Cloning: A Laboratory Manual, Cold Spring Harbor I.B.R.), the cells being plated out on LB agar (Lennox, 1955, Virology, 1:190 I.B.R.)+100 µg/ml ampicillin. After incubation overnight at 37° C., recombinant individual clones were selected.

EXAMPLE 2

Isolation and Sequencing of the dep34 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02 I.B.R.). The DNA fragments were dephosphorylated with shrimp alkaline phosphatase (Roche Molecular Biochemicals, Mannheim, Germany, Product Description SAP, Product No. 1758250 I.B.R.). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01 I.B.R.) was cleaved with the restriction enzyme BamHI (Amersham Pharmacia, Freiburg, Germany, Product Description BamHI, Product No. 27-0868-04 I.B.R.). The ligation of the cosmid fragments in the sequencing vector pZero-1 was carried out as described by Sambrook et al. (1989, Molecular Cloning: A Laboratory Manual, Cold Spring Harbor) I.B.R., the DNA mixture being incubated overnight with T4 ligase (Pharmacia Biotech, Freiburg, Germany). This ligation mixture was then electroporated (Tauch et al. 1994, FEMS Microbiol. Letters, 123:343–7 I.B.R.) into the E. coli strain DH5αmcr (Grant, 1990, Proceedings of the National Academy of Sciences, U.S.A., 87:4645–4649 I.B.R.). Letters, 123:343–7) and plated out on LB agar (Lennox, 1955, Virology, 1:190 I.B.R.) with 50 µg/ml zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467 I.B.R.) with modifications according to Zimmermann et al. (1990, Nucleic Acids Research, 18:1067 I.B.R.). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231 I.B.R.) version 97-0. The individual sequences of the pzero1 derivatives were assembled to a continuous contig. The computer-assisted coding region analyses were prepared with the XNIP program (Staden, 1986, Nucleic Acids Research, 14:217–231 I.B.R.). Further analyses were carried out with the "BLAST search program" (Altschul et al., 1997, Nucleic Acids Research, 25:3389–3402 I.B.R.) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 1650 bp, which was called the dep34 gene. The dep34 gene codes for a polypeptide of 549 amino acids.

EXAMPLE 3

Preparation of an Integration Vector for Integration Mutagenesis of the dep34 Gene From the strain ATCC 13032, chromosomal DNA was isolated by the method of Eikmanns et al. (Microbiology 140: 1817–1828 (1994)) I.B.R. On the basis of the sequence of the dep34 gene known for C. glutamicum from example 2, the following oligonucleotides were chosen for the polymerase chain reaction (see SEQ ID No. 3 and SEQ ID No. 4):

```
dep34-int1:
  5' CTG TGC TGC TGA AAC TTC C 3'    SEQ ID NO:3 dep34-int2:
  5' AGT CCA ATG AGA GCC AAG C 3'    SEQ ID NO:4
```

The primers shown were synthesized by MWG Biotech (Ebersberg, Germany) and the PCR reaction was carried out by the standard PCR method of Innis et al. (PCR protocols. A guide to methods and applications, 1990, Academic Press I.B.R.) with the Taq-polymerase from Boehringer Mannheim (Germany, Product Description Taq DNA polymerase, Product No. 1 146 165). With the aid of the polymerase chain reaction, the primers allow amplification of an internal fragment of the dep34 gene 541 bp in size. The product amplified in this way was tested electrophoretically in a 0.8% agarose gel.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663 I.B.R.).

The E. coli strain TOP10 was then electroporated with the ligation batch (Hanahan, In: DNA cloning. A practical approach. Vol. I. IRL-Press, Oxford, Washington D.C., USA, 1985 I.B.R.). Selection of plasmid-carrying cells was carried out by plating out the transformation batch on LB Agar (Sambrook et al., Molecular cloning: a laboratory manual. 2$^{nd}$ Ed. Cold Spring Harbor Laboratory Press, Cold Spring Harbor, N.Y., 1989 I.B.R.), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1dep34int and is shown in FIG. 1.

EXAMPLE 4

Integration Mutagenesis of the dep34 Gene in the Strain DSM 5715

The vector pCR2.1dep34int mentioned in example 3 was electroporated by the electroporation method of Tauch et al.(FEMS Microbiological Letters, 123:343–347 (1994) I.B.R.) in *Corynebacterium glutamicum* DSM 5715. The strain DSM 5715 is an AEC-resistant lysine producer. The vector pCR2.1dep34int cannot replicate independently in DSM5715 and is retained in the cell only if it has integrated into the chromosome of DSM 5715. Selection of clones with pCR2.1dep34int integrated into the chromosome was carried out by plating out the electroporation batch on LB agar (Sambrook et al., Molecular cloning: a laboratory manual. 2$^{nd}$ Ed. Cold Spring Harbor Laboratory Press, Cold Spring Harbor, N.Y. I.B.R.), which had been supplemented with 15 mg/l kanamycin.

For detection of the integration, the dep34int fragment was labeled with the Dig hybridization kit from Boehringer by the method of "The DIG System Users Guide for Filter Hybridization" of Boehringer Mannheim GmbH (Mannheim, Germany, 1993 I.B.R.). Chromosomal DNA of a potential integrant was isolated by the method of Eikmanns et al. (Microbiology 140: 1817–1828 (1994) I.B.R.) and in each case cleaved with the restriction enzymes KpnI, EcoRI and PstI. The fragments formed were separated by means of agarose gel electrophoresis and hybridized at 68° C. with the Dig hybridization kit from Boehringer. The plasmid pCR2.1dep34int mentioned in example 3 had been inserted into the chromosome of DSM5715 within the chromosomal dep34 gene. The strain was called DSM5715::pCR2.1dep34int.

EXAMPLE 5

Preparation of Lysine

The *C. glutamicum* strain DSM5715::pCR2.1dep34int obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

|  | Medium Cg III |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1 OD. Medium MM was used for the main culture.

|  | Medium MM |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution are brought to pH 7 with aqueous ammonia and autoclaved. The sterile substrate and vitamin solutions are then added, and the $CaCO_3$ autoclaved in the dry state is added.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Lysine HCl g/l |
|---|---|---|
| DSM5715 | 8.7 | 12.64 |
| DSM5715::pCR2.1dep34int | 9.1 | 14.14 |

This application claims priority to German Priority Document Application No. 100 44 708.2, filed on Sep. 9, 2000 and to German Priority Document Application No. 101 12 429.5, filed on Mar. 15, 2001. Both German Priority Documents are hereby incorporated by reference in their entirety.

We claim:

1. An isolated polynucleotide comprising the nucleotide sequence of SEQ ID NO: 1.

2. An isolated polynucleotide comprising the complete complement of the nucleotide sequence of SEQ ID NO: 1.

3. A vector comprising the isolated polynucleotide of claim 1.

4. An *Escherichia coli* comprising the isolated polynucleotide of claim 1.

5. The vector pCR2.1 dep34int deposited under DSM14144.

* * * * *

SEQUENCE LISTING

<160> NUMBER OF SEQ ID NOS: 4

<210> SEQ ID NO 1
<211> LENGTH: 2120
<212> TYPE: DNA
<213> ORGANISM: Corynebacterium glutamicum

```
<220> FEATURE:
<221> NAME/KEY: CDS
<222> LOCATION: (259)..(1905)
<223> OTHER INFORMATION:

<400> SEQUENCE: 1
acatttcgcc aggttccacc aagcacgcga agggctagaa cacctaattg ttgagtactt        60
cgaaaaatgg ccaggctccc aacatctaga tgagcctgca gatcgagaag caatcgccat       120
agttggcctg ctgatctcgg tcatgcttca aggttctcgt gaatggcacg acatgccaca       180
aggcacgcaa gctgatttcc aagcctgctg tcgcaaagca attaaaaata cttttcttct       240
tagaggtgga ttttcaga atg aca tca cag gtc aag ccg gac gac gaa cgt         291
                    Met Thr Ser Gln Val Lys Pro Asp Asp Glu Arg
                     1               5                  10 ccg gta aca aca att tca aaa agt ggt gca cct tcg gcc cac acc tca         339
Pro Val Thr Thr Ile Ser Lys Ser Gly Ala Pro Ser Ala His Thr Ser
            15                  20                  25 gca cca tat ggt gca gca gca act gaa gaa gct gtc gag gaa aaa acc         387
Ala Pro Tyr Gly Ala Ala Ala Thr Glu Glu Ala Val Glu Glu Lys Thr
        30                  35                  40 aaa ggt cgc gtt gga ttt atc atc gca gcc ctc atg ttg gcg atg ctt         435
Lys Gly Arg Val Gly Phe Ile Ile Ala Ala Leu Met Leu Ala Met Leu
 45                  50                  55 ctt agc tcc ttg ggt cag acc att ttc ggt tct gcc ctg cca acg att         483
Leu Ser Ser Leu Gly Gln Thr Ile Phe Gly Ser Ala Leu Pro Thr Ile
 60                  65                  70                  75 gtt ggt gag ctt ggc ggc gtt aac cac atg acc tgg gtg att acc gcc         531
Val Gly Glu Leu Gly Gly Val Asn His Met Thr Trp Val Ile Thr Ala
             80                  85                  90 ttc ctc ttg ggc cag acc att tca ttg cct att ttc ggc aag ttg ggt         579
Phe Leu Leu Gly Gln Thr Ile Ser Leu Pro Ile Phe Gly Lys Leu Gly
         95                 100                 105 gac cag ttt ggt cgc aaa tac ctc ttc atg ttt gcc atc gca ctg ttc         627
Asp Gln Phe Gly Arg Lys Tyr Leu Phe Met Phe Ala Ile Ala Leu Phe
    110                 115                 120 gtg gtg ggt tcc atc atc ggt gct ttg gct cag aac atg acc acc ttg         675
Val Val Gly Ser Ile Ile Gly Ala Leu Ala Gln Asn Met Thr Thr Leu
125                 130                 135 att gtg gct cgt gca ctg cag ggt atc gcc ggt ggt ggc ttg atg att         723
Ile Val Ala Arg Ala Leu Gln Gly Ile Ala Gly Gly Gly Leu Met Ile
140                 145                 150                 155 ctt tct cag gca att acc gct gat gtc acc acc gcc cgt gag cgt gca         771
Leu Ser Gln Ala Ile Thr Ala Asp Val Thr Thr Ala Arg Glu Arg Ala
                160                 165                 170 aag tac atg ggc atc atg ggt tcc gtt ttc gga ctg tcc tcc atc ctt         819
Lys Tyr Met Gly Ile Met Gly Ser Val Phe Gly Leu Ser Ser Ile Leu
            175                 180                 185 ggc cca ttg ctt ggt ggc tgg ttc act gac ggt cca ggc tgg cgt tgg         867
Gly Pro Leu Leu Gly Gly Trp Phe Thr Asp Gly Pro Gly Trp Arg Trp
        190                 195                 200 ggt ctg tgg ttg aac gtt cca atc ggc atc atc gca ctg gtt gct atc         915
Gly Leu Trp Leu Asn Val Pro Ile Gly Ile Ile Ala Leu Val Ala Ile
    205                 210                 215 gct gtg ctg ctg aaa ctt cca gct cgt gaa cgt ggc aag gtc tcc gtt         963
Ala Val Leu Leu Lys Leu Pro Ala Arg Glu Arg Gly Lys Val Ser Val
220                 225                 230                 235 gac tgg ttg gga agc atc ttc atg gct atc gcc acc acc gca ttt gtc        1011
Asp Trp Leu Gly Ser Ile Phe Met Ala Ile Ala Thr Thr Ala Phe Val
                240                 245                 250
```

```
ctc gca gtg acc tgg ggt ggc aat gaa tat gag tgg gca tca cca atg       1059
Leu Ala Val Thr Trp Gly Gly Asn Glu Tyr Glu Trp Ala Ser Pro Met
            255                 260                 265 atc atc ggt ttg ttc atc acg aca ttg gtc gct gcg ata gtg ttc gtt       1107
Ile Ile Gly Leu Phe Ile Thr Thr Leu Val Ala Ala Ile Val Phe Val
            270                 275                 280 ttc gtc gaa aag cgt gct gtt gac cca ctg gtc ccc atg ggc ctt ttc       1155
Phe Val Glu Lys Arg Ala Val Asp Pro Leu Val Pro Met Gly Leu Phe
        285                 290                 295 tcg aac cgc aac ttc gtg ctc acc gcc gtc gcc ggt atc ggc gta ggc       1203
Ser Asn Arg Asn Phe Val Leu Thr Ala Val Ala Gly Ile Gly Val Gly
300                 305                 310                 315 ctg ttt atg atg ggc acc atc gcg tac atg cct acc tac ctg cag atg       1251
Leu Phe Met Met Gly Thr Ile Ala Tyr Met Pro Thr Tyr Leu Gln Met
                320                 325                 330 gtt cat ggt ctg aac cca acg caa gct ggt ctg atg ctg atc cca atg       1299
Val His Gly Leu Asn Pro Thr Gln Ala Gly Leu Met Leu Ile Pro Met
                    335                 340                 345 atg atc ggc ctg att ggt aca tcc act gtg gtg ggc aac atc gtg tcc       1347
Met Ile Gly Leu Ile Gly Thr Ser Thr Val Val Gly Asn Ile Val Ser
        350                 355                 360 aag act ggc aag tac aag tgg tac cca ttc atc ggc atg ctc atc atg       1395
Lys Thr Gly Lys Tyr Lys Trp Tyr Pro Phe Ile Gly Met Leu Ile Met
365                 370                 375 gtc ctt gcc cta gta ctg cta tcg acg ctg aca cct tcg gca agc ttg       1443
Val Leu Ala Leu Val Leu Leu Ser Thr Leu Thr Pro Ser Ala Ser Leu
380                 385                 390                 395 gct ctc att gga ctg tac ttc ttc gtc ttc gga ttc ggc ctg ggc tgt       1491
Ala Leu Ile Gly Leu Tyr Phe Phe Val Phe Gly Phe Gly Leu Gly Cys
                400                 405                 410 gca atg cag att ttg gtt ctc atc gtg cag aac tcc ttc cca atc acc       1539
Ala Met Gln Ile Leu Val Leu Ile Val Gln Asn Ser Phe Pro Ile Thr
                    415                 420                 425 atg gtt ggc acc gcg acc ggt tcc aac aac ttc ttc cgc caa atc ggt       1587
Met Val Gly Thr Ala Thr Gly Ser Asn Asn Phe Phe Arg Gln Ile Gly
        430                 435                 440 gga gca gta ggt tcc gca ctg atc ggt ggc ctg ttt atc tcc aac ctg       1635
Gly Ala Val Gly Ser Ala Leu Ile Gly Gly Leu Phe Ile Ser Asn Leu
445                 450                 455 tcc gac cga ttc acc gaa aac gtc ccc gca gca gtg gct tcc atg ggt       1683
Ser Asp Arg Phe Thr Glu Asn Val Pro Ala Ala Val Ala Ser Met Gly
460                 465                 470                 475 gaa gaa ggc gca caa tac gcc tca gca atg tcc gat ttc tcc ggt gca       1731
Glu Glu Gly Ala Gln Tyr Ala Ser Ala Met Ser Asp Phe Ser Gly Ala
                480                 485                 490 tcc aac ctc act cca cac ctt gtt gaa tca ctt cca caa gca ctc cgt       1779
Ser Asn Leu Thr Pro His Leu Val Glu Ser Leu Pro Gln Ala Leu Arg
                    495                 500                 505 gaa gca att caa ctt tct tac aac gac gcc ctg aca cca atc ttc ttg       1827
Glu Ala Ile Gln Leu Ser Tyr Asn Asp Ala Leu Thr Pro Ile Phe Leu
        510                 515                 520 gcg ctc acc ccg atc gca gta gtc gcc gcg atc ctc ctc ttt ttc atc       1875
Ala Leu Thr Pro Ile Ala Val Val Ala Ala Ile Leu Leu Phe Phe Ile
525                 530                 535 cgt gaa gat cac ctc aag gaa acg cac gaa taatgacaca cgaaacttcc         1925
Arg Glu Asp His Leu Lys Glu Thr His Glu
540                 545 gtccccggac ctgccgacgc gcaggtcgca ggagatacga agctgcgcaa aggccgcgcg     1985
aagaaggaaa aaactccttc atcaatgacg cctgaacaac aaaagaaagt ctggtgggtc     2045
```

```
ctcagcgcgc tgatggtcgc catgatgatg gcctcccttg accagatgat tttcggcaca    2105
gccctgccaa caatc                                                     2120
```

<210> SEQ ID NO 2
<211> LENGTH: 549
<212> TYPE: PRT
<213> ORGANISM: Corynebacterium glutamicum

<400> SEQUENCE: 2

```
Met Thr Ser Gln Val Lys Pro Asp Asp Glu Arg Pro Val Thr Thr Ile
1               5                   10                  15

Ser Lys Ser Gly Ala Pro Ser Ala His Thr Ser Ala Pro Tyr Gly Ala
            20                  25                  30

Ala Ala Thr Glu Glu Ala Val Glu Lys Thr Lys Gly Arg Val Gly
        35                  40                  45

Phe Ile Ile Ala Ala Leu Met Leu Ala Met Leu Leu Ser Ser Leu Gly
    50                  55                  60

Gln Thr Ile Phe Gly Ser Ala Leu Pro Thr Ile Val Gly Glu Leu Gly
65                  70                  75                  80

Gly Val Asn His Met Thr Trp Val Ile Thr Ala Phe Leu Leu Gly Gln
                85                  90                  95

Thr Ile Ser Leu Pro Ile Phe Gly Lys Leu Gly Asp Gln Phe Gly Arg
            100                 105                 110

Lys Tyr Leu Phe Met Phe Ala Ile Ala Leu Phe Val Val Gly Ser Ile
        115                 120                 125

Ile Gly Ala Leu Ala Gln Asn Met Thr Thr Leu Ile Val Ala Arg Ala
    130                 135                 140

Leu Gln Gly Ile Ala Gly Gly Gly Leu Met Ile Leu Ser Gln Ala Ile
145                 150                 155                 160

Thr Ala Asp Val Thr Thr Ala Arg Glu Arg Ala Lys Tyr Met Gly Ile
                165                 170                 175

Met Gly Ser Val Phe Gly Leu Ser Ser Ile Leu Gly Pro Leu Leu Gly
            180                 185                 190

Gly Trp Phe Thr Asp Gly Pro Gly Trp Arg Trp Gly Leu Trp Leu Asn
        195                 200                 205

Val Pro Ile Gly Ile Ile Ala Leu Val Ala Ile Ala Val Leu Leu Lys
    210                 215                 220

Leu Pro Ala Arg Glu Arg Gly Lys Val Ser Val Asp Trp Leu Gly Ser
225                 230                 235                 240

Ile Phe Met Ala Ile Ala Thr Thr Ala Phe Val Leu Ala Val Thr Trp
                245                 250                 255

Gly Gly Asn Glu Tyr Glu Trp Ala Ser Pro Met Ile Ile Gly Leu Phe
            260                 265                 270

Ile Thr Thr Leu Val Ala Ala Ile Val Phe Val Phe Val Glu Lys Arg
        275                 280                 285

Ala Val Asp Pro Leu Val Pro Met Gly Leu Phe Ser Asn Arg Asn Phe
    290                 295                 300

Val Leu Thr Ala Val Ala Gly Ile Gly Val Gly Leu Phe Met Met Gly
305                 310                 315                 320

Thr Ile Ala Tyr Met Pro Thr Tyr Leu Gln Met Val His Gly Leu Asn
                325                 330                 335

Pro Thr Gln Ala Gly Leu Met Leu Ile Pro Met Met Ile Gly Leu Ile
            340                 345                 350
```

```
Gly Thr Ser Thr Val Val Gly Asn Ile Val Ser Lys Thr Gly Lys Tyr
            355                 360                 365

Lys Trp Tyr Pro Phe Ile Gly Met Leu Ile Met Val Leu Ala Leu Val
    370                 375                 380

Leu Leu Ser Thr Leu Thr Pro Ser Ala Ser Leu Ala Leu Ile Gly Leu
385                 390                 395                 400

Tyr Phe Phe Val Phe Gly Phe Leu Gly Cys Ala Met Gln Ile Leu
                405                 410                 415

Val Leu Ile Val Gln Asn Ser Phe Pro Ile Thr Met Val Gly Thr Ala
            420                 425                 430

Thr Gly Ser Asn Asn Phe Phe Arg Gln Ile Gly Gly Ala Val Gly Ser
            435                 440                 445

Ala Leu Ile Gly Gly Leu Phe Ile Ser Asn Leu Ser Asp Arg Phe Thr
    450                 455                 460

Glu Asn Val Pro Ala Ala Val Ala Ser Met Gly Glu Glu Gly Ala Gln
465                 470                 475                 480

Tyr Ala Ser Ala Met Ser Asp Phe Ser Gly Ala Ser Asn Leu Thr Pro
                485                 490                 495

His Leu Val Glu Ser Leu Pro Gln Ala Leu Arg Glu Ala Ile Gln Leu
            500                 505                 510

Ser Tyr Asn Asp Ala Leu Thr Pro Ile Phe Leu Ala Leu Thr Pro Ile
            515                 520                 525

Ala Val Val Ala Ala Ile Leu Leu Phe Phe Ile Arg Glu Asp His Leu
            530                 535                 540

Lys Glu Thr His Glu
545

<210> SEQ ID NO 3
<211> LENGTH: 19
<212> TYPE: DNA
<213> ORGANISM: Corynebacterium glutamicum

<400> SEQUENCE: 3
ctgtgctgct gaaacttcc                                                19

<210> SEQ ID NO 4
<211> LENGTH: 19
<212> TYPE: DNA
<213> ORGANISM: Corynebacterium glutamicum

<400> SEQUENCE: 4
agtccaatga gagccaagc                                                19
```